(12) United States Patent
Hung et al.

(10) Patent No.: US 11,547,213 B2
(45) Date of Patent: Jan. 10, 2023

(54) SEAT CUSHION

(71) Applicant: ASUSTeK COMPUTER INC., Taipei (TW)

(72) Inventors: Shao-Wei Hung, Taipei (TW); Tzu-Hsuan Hsia, Taipei (TW); Ming-Jui Jin, Taipei (TW)

(73) Assignee: ASUSTEK COMPUTER INC., Taipei (TW)

(*) Notice: Subject to any disclaimer, the term of this patent is extended or adjusted under 35 U.S.C. 154(b) by 338 days.

(21) Appl. No.: 16/801,338

(22) Filed: Feb. 26, 2020

(65) Prior Publication Data
US 2020/0281364 A1 Sep. 10, 2020

(30) Foreign Application Priority Data

Mar. 6, 2019 (TW) ................................. 108107513

(51) Int. Cl.
A47C 7/72 (2006.01)
G06T 7/593 (2017.01)
G01B 11/25 (2006.01)
G01S 17/08 (2006.01)

(52) U.S. Cl.
CPC ................ A47C 7/72 (2013.01); G01B 11/25 (2013.01); G01S 17/08 (2013.01); G06T 7/593 (2017.01); G06T 2207/10012 (2013.01)

(58) Field of Classification Search
CPC .. A47C 7/72; A47C 9/00; G06T 7/593; G01B 11/25
See application file for complete search history.

(56) References Cited

U.S. PATENT DOCUMENTS

| 6,353,394 | B1 | 3/2002 | Maeda et al. |
| 9,795,322 | B1 | 10/2017 | Karunaratne et al. |
| 10,568,547 | B1* | 2/2020 | Johanning ............... A61B 5/224 |
| 10,926,662 | B2* | 2/2021 | Maguire ................ B60N 2/002 |
| 11,045,145 | B2* | 6/2021 | Aoki ........................ A61B 5/08 |

(Continued)

FOREIGN PATENT DOCUMENTS

| CN | 107082034 A | 8/2017 |
| CN | 206975805 U | 2/2018 |

(Continued)

OTHER PUBLICATIONS eESR issued in corresponding European patent application No. 20159470.2-1011 dated Apr. 22, 2020.

Primary Examiner — Rowina J Cattungal
(74) Attorney, Agent, or Firm — McClure, Qualey & Rodack, LLP

(57) ABSTRACT

A seat cushion is provided. The seat cushion includes an upper pad, a lower pad, a support structure, a plurality of optical modules, and a processor. The upper pad includes a plurality of transparent areas. The lower pad is provided with a plurality of grooves to accommodate the optical modules. The support structure is connected between the upper pad and the lower pad. The optical modules are located below the upper pad and are disposed corresponding to the transparent areas. The optical modules respectively transmit sense signals and respectively receive feedback signals corresponding to the sense signals. The processor is coupled to the optical modules and is configured to collect optical signals.

13 Claims, 4 Drawing Sheets

(56) References Cited

U.S. PATENT DOCUMENTS

| | | | |
|---|---|---|---|
| 2002/0167486 A1* | 11/2002 | Tan | A61B 5/1116 |
| | | | 345/156 |
| 2004/0007681 A1* | 1/2004 | Moisei | G01V 8/20 |
| | | | 250/221 |
| 2006/0152378 A1 | 7/2006 | Lokhorst et al. | |
| 2006/0155442 A1* | 7/2006 | Luo | B60R 21/01538 |
| | | | 701/45 |
| 2007/0289800 A1* | 12/2007 | Aoki | G06T 7/74 |
| | | | 180/271 |
| 2008/0061989 A1* | 3/2008 | Yasunori | B60R 21/0152 |
| | | | 340/650 |
| 2015/0196209 A1 | 7/2015 | Morris et al. | |
| 2016/0089031 A1 | 3/2016 | Hu | |
| 2016/0183687 A1 | 6/2016 | Hoyt et al. | |

FOREIGN PATENT DOCUMENTS

| | | |
|---|---|---|
| CN | 108634658 A | 10/2018 |
| JP | 2005532854 A | 11/2005 |
| JP | 2017535316 A | 11/2017 |
| WO | 03100741 A1 | 12/2003 |

* cited by examiner

SEAT CUSHION

CROSS-REFERENCE TO RELATED APPLICATION

This application claims the priority benefit of Taiwan Application Serial No. 108107513, filed on Mar. 6, 2019. The entirety of the above-mentioned patent application is hereby incorporated by reference herein and made a part of specification.

BACKGROUND OF THE INVENTION

Field of the Invention

The disclosure relates to a seat cushion.

Description of the Related Art

To ensure users to keep appropriate sitting postures on a seat cushion, types of seat cushions are increasingly diversified and functionalized. Therefore, posture sensing features are also applied to the seat cushion.

Generally, a pressure sensor is disposed in a seat cushion to sense pressure exerted by a user when the user sits on the seat cushion and determines whether a sitting posture of the user is appropriate. However, measurement data misalignment of the pressure sensor occurs when the cushion materials are worn out or a sensitivity of the pressure sensor decreases due to long-term usage of the seat cushion.

BRIEF SUMMARY OF THE INVENTION

According to an aspect of the disclosure, a seat cushion includes an upper pad, a lower pad, a support structure, a plurality of optical modules, and a processor. The upper pad includes a plurality of transparent areas. The optical modules are located below the upper pad and are disposed corresponding to the transparent areas. The optical modules respectively receive an optical signal. The lower pad is provided with a plurality of grooves to accommodate the optical modules. The support structure is connected between the upper pad and the lower pad. The processor is coupled to the optical modules and is configured to collect the optical signals.

In conclusion, for the seat cushion according to the disclosure, users sitting postures are detected by the optical modules, that is, the optical modules transmit sense signals and receive optical signals corresponding to the sense signals to sense the sitting posture. Therefore, measurement accuracy is not affected by material aging of the seat cushion.

DETAILED DESCRIPTION OF THE EMBODIMENTS

The disclosure relates to a seat cushion. Although a plurality of patterns considered as preferable patterns for implementing the disclosure is described in this specification, it should be understood that the disclosure is still implemented in a plurality of manners and should not be limited to the following specific embodiments or specific manners for implementing the following features. In another case, well-known details are not described or discussed again to avoid blur of key points of the disclosure.

In the disclosure, a word "coupled" and a derivative word thereof are used. In some embodiments, "coupled" is used to represent that two or more elements are in direct contact with each other physically or electrically, or means that two or more elements are in indirect contact with each other electrically. The word "coupled" is further used to represent that two or more elements cooperate or interact with each other.

Figure 1:
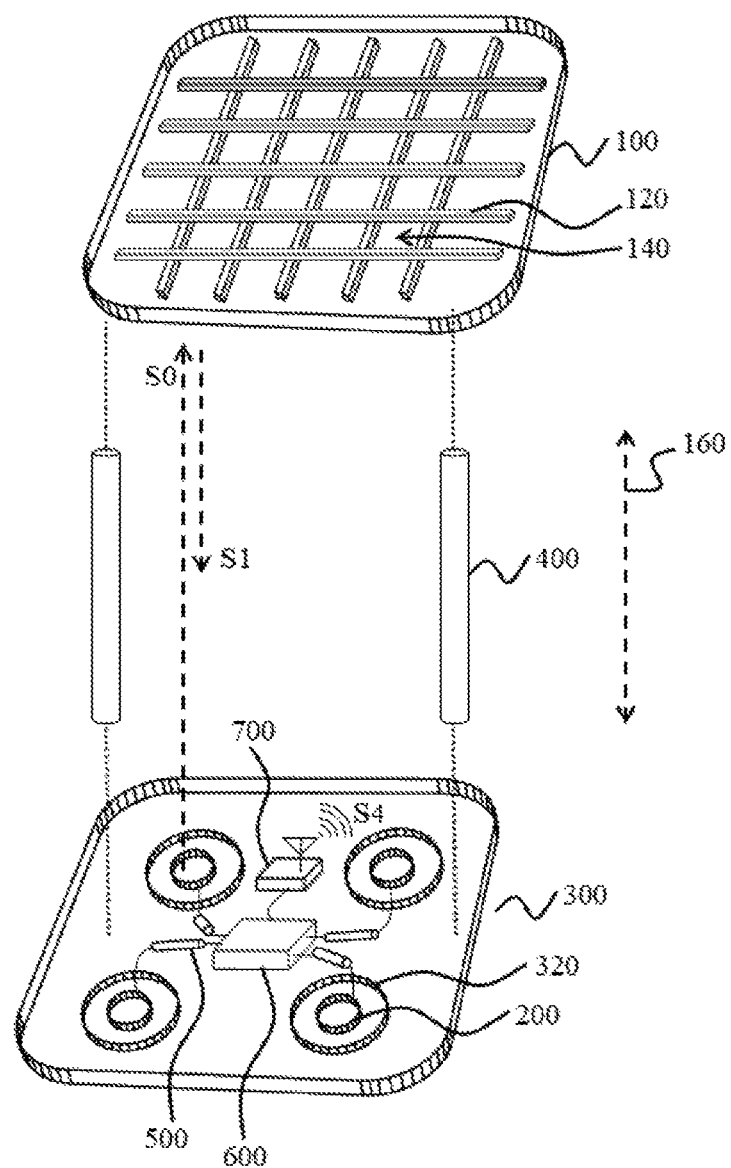
FIG. 1 is a schematic diagram of a seat cushion according to some embodiments of the disclosure.

FIG. 1 is a schematic diagram of a seat cushion 10 according to some embodiments of the disclosure. Referring to FIG. 1, in some embodiments, the seat cushion 10 is but not limited to a chair cushion, a yoga mat, a mattress, or any cushion that is suitable for a user to sit on, to lie on, or to lean on. The chair cushion is used as an example for a subsequent description. In an embodiment, the seat cushion 10 is a chair cushion with mesh structure. The mesh structure allows light to pass through the chair cushion.

Referring to FIG. 1, in some embodiments, the seat cushion 10 includes an upper pad 100, a lower pad 300, a support structure 400, a plurality of optical modules 200, a processor 600, a conversion circuit 500, and a communications module 700. The lower pad 300 has a plurality of grooves 320 to accommodate the optical modules 200. The support structure 400 is connected between the upper pad 100 and the lower pad 300. The optical modules 200 are located below the upper pad 100 and are disposed corresponding to the transparent areas 140. The processor 600 is coupled between the optical modules 200 and the communications module 700. In other embodiment, the conversion circuit 500 is coupled between the optical modules 200 and the processor 600.

Based on the foregoing description, in an embodiment, the upper pad 100 contacts the user. The upper pad 100 has a normal direction 160 and includes a main body area 120 and a plurality of transparent areas 140. The transparent areas 140 are disposed in a hollow portion of the main body area 120. Specifically, the transparent areas 140 of the upper pad 100 are transparent in the normal direction 160, that is, light passes through the transparent areas 140 from top to bottom or from bottom to top. In an embodiment, the main body area 120 is a mesh structure. In other embodiment, the material of the main body area 120 is but not limited to plastic, fabric, metal, wood, or a material used for supporting and fixing. In an embodiment, the transparent area 140 is an opening area or a transparent substance, and a material of the transparent area 140 is but not limited to plastic or another transparent material. In an embodiment, when the transparent area 140 is an opening area, the upper pad 100 bears a weight of the user by the main body area 120. When the transparent area 140 is a transparent substance, the transparent area 140 also bears the weight of the user.

In some embodiments, the lower pad 300 is disposed on a horizontal plane, and the upper pad 100 is disposed on another horizontal plane. The optical modules 200 are disposed on the lower pad 300 and the two horizontal planes are both perpendicular to the normal direction 160.

Figure 2:
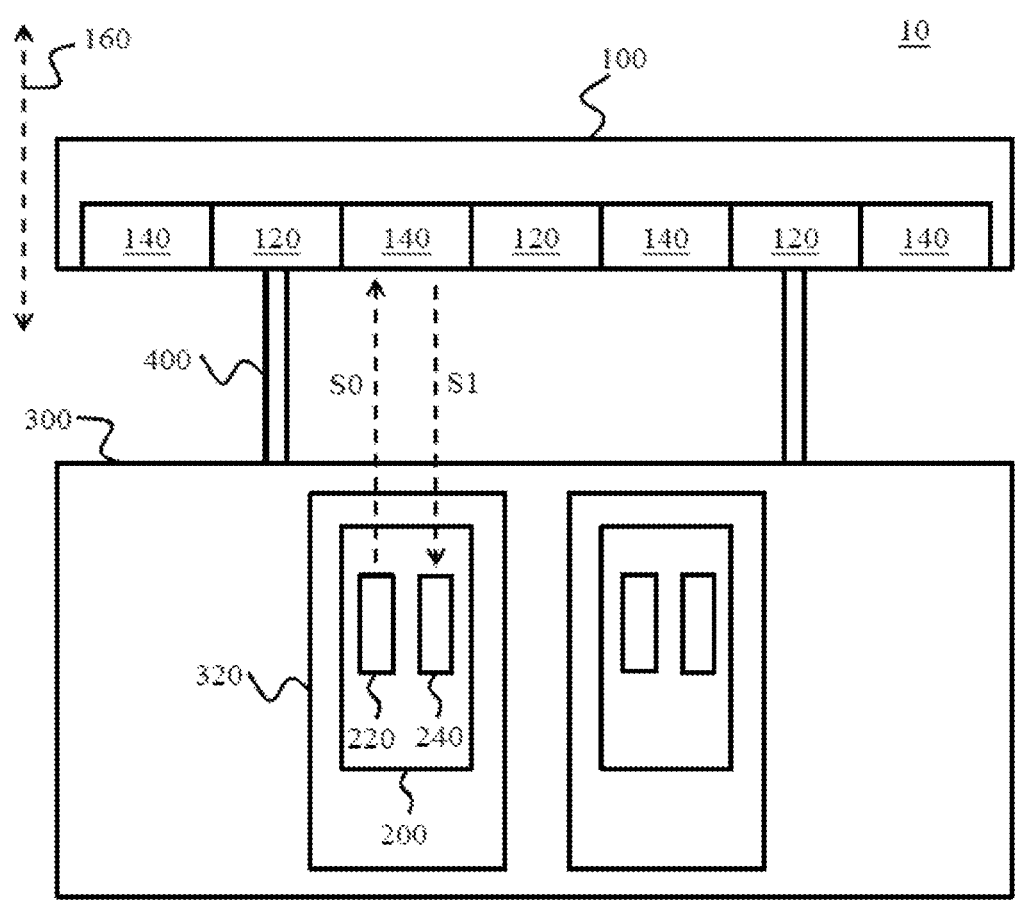
FIG. 2 is a cross-sectional view of a seat cushion according to some embodiments of the disclosure.

FIG. 2 is a cross-sectional view of a seat cushion 10 according to some embodiments of the disclosure. Referring to FIG. 2, in an embodiment, the optical modules 200 are disposed below the upper pad 100 and are corresponding to the transparent areas 140 in the normal direction 160. Therefore, the optical modules 200 directly sense an object (such as buttocks of the user located on the upper pad 100 without being affected by interference from the material and a thickness of the main body area 120.

Based on the foregoing description, in an embodiment, each optical module 200 respectively receives an optical signal S1. In some embodiments, a sense signal S0 is transmitted from the optical module 200 and passes through the transparent area 140 to the object such as the buttocks of the user. When the sense signal S0 is transmitted to the user, the optical signal S1 corresponding to the sense signal S0 is generated and reflected, and then the optical signal S1 passes through the transparent area 140 to the optical module 200. In an embodiment, the sense signal S0 and the optical signal S1 are lasers, infrared light, or other light not interfered by visible light. It should be particularly noted that when the optical module 200 receives the optical signal S1, the optical module 200 converts the optical signal S1 in an optical form into an optical signal S1 in a digital form or an analog form.

In an embodiment, the optical modules 200 respectively include a transmitter 220 and a receiver 240, and the transmitter 220 and the receiver 240 face a transparent area 140 of the upper pad 100. The transmitter 220 is configured to transmit the sense signal S0 to an object such as the buttocks of the user, and the receiver 240 is configured to receive the optical signal S1 that is corresponding to the sense signal S0 and reflected by the object.

In some embodiments, the optical module 200 is a time of flight (TOF) sensor, referred to as a TOF sensing module. The transmitter 220 is an infrared light emitting diode (IR LED) or a vertical-cavity surface-emitting laser (VCSEL). In this embodiment, the processor 600 detects a first flight time and a second flight time by using the optical module 200 as a distance parameter between the TOF sensors and the object, where the first flight time is a time required by transmitting the sense signals S0 from the transmitter 220 to the object (the buttocks of the user) and the second flight time is a time required by reflecting the optical signals from the object to the optical module 200.

In an embodiment, the optical module 200 is a structured light sensor, and the transmitter 220 is an IR LED or a VCSEL. In this embodiment, the sense signal S0 and the optical signal S1 are patterns with specific shape. In this embodiment, the processor 600 analyzes a difference between the pattern of the sense signal S0 and the pattern of the optical signal S1 by an algorithm, to obtain depth information between the structured light sensor (the optical module 200) and the object as a distance parameter.

In an embodiment, the optical module 200 is a proximity sensor, and the transmitter 220 is an IR LED or a VCSEL. In this embodiment, the processor 600 analyzes a difference between light energy of the sense signal S0 and light energy of the optical signal S1, to obtain a distance parameter between the proximity sensor and the object.

In some embodiments, the optical module 200 is a stereo vision camera module. Specifically, the receiver 240 is an image capture element and is configured to capture image information (that is, the optical signal S1) from the object. The stereo vision camera module includes two or more image capture elements, configured to capture the image information of the object from different angles. The processor 600 performs an operation on the image information by a triangulation method to obtain a distance parameter between the stereo vision camera module 200 and the object.

Referring to FIG. 2, in an embodiment, the support structure 400 is configured to support the upper pad 100 to maintain a fixed distance between a portion of the main body area 120 and the lower pad 300. Therefore, the upper pad 100 is not compressed to touch the lower pad 300 because the upper pad 100 bears the weight of the user. It should be particularly noted that the portion of the main body area 120 refers to a portion connected to the support structure 400. Another portion of the main body area 120 that is not connected to the support structure 400 is deformable. Therefore, a distance between another portion of the main body area 120 without connected to the support structure 400 and the lower pad 300 is not fixed.

Figure 3:
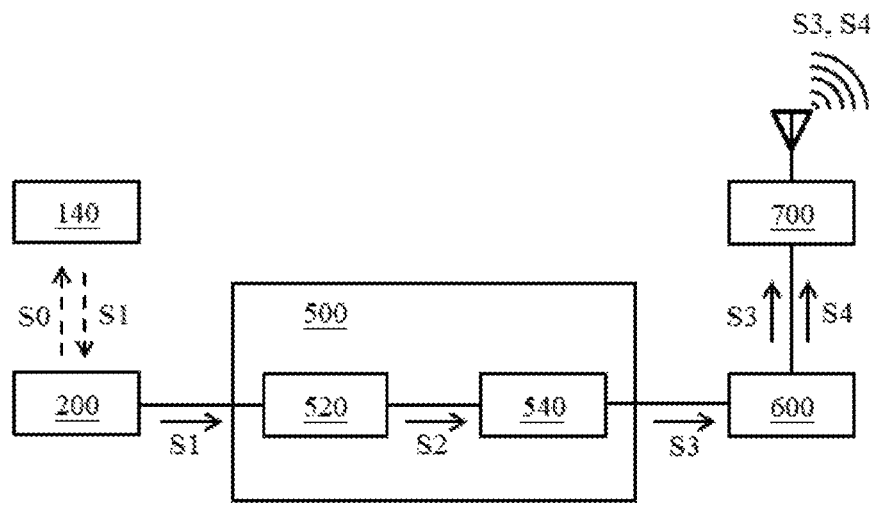
FIG. 3 is a signal diagram according to some embodiments of the disclosure.

FIG. 3 is a signal diagram according to some embodiments of the disclosure. Referring to FIG. 3, in an embodiment, the conversion circuit 500 includes a plurality of amplification circuits 520 and a plurality of analog-to-digital circuits 540. The amplification circuits 520 are respectively coupled to the optical modules 200, and the analog-to-digital circuits 540 are respectively coupled to the amplification circuits 520 and the processor 600. The amplification circuit 520 is configured to amplify the optical signal S1 into an amplification signal S2, and the analog-to-digital circuit 540 is configured to convert the amplification signal S2 into a digital optical signal S3, and to transmit the digital optical signal S3 to the processor 600. That is, when the optical signal S1 is in an analog form, the optical signal S1 needs to be converted into the digital optical signal S3 through the conversion circuit 500, so that the digital optical signal S3 is collected by the processor 600.

In an embodiment, a circuit connection relationship between the optical modules 200, the plurality of amplification circuits 520, and the plurality of analog-to-digital circuits 540 is not limited to one-by-one connection. That is, the circuit connection relationship there between is a plurality of optical modules 200 corresponding to one conversion circuits 500, a plurality of amplification circuits 520 corresponding to one conversion circuits 500, or another connection form.

Figure 4:
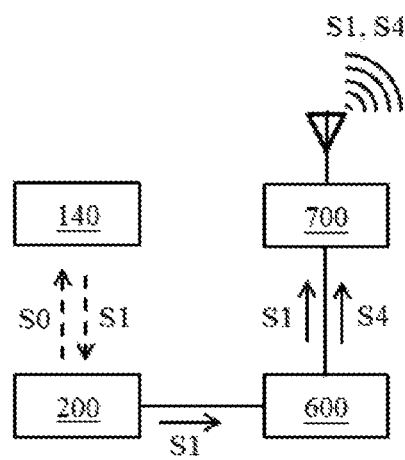
FIG. 4 is a signal diagram according to some embodiments of the disclosure.

FIG. 4 is a signal diagram according to some embodiments of the disclosure. Referring to FIG. 4, it is to be noted that in some embodiments, when the optical signal S1 is in a digital form, the conversion circuit 500 is not a requirement. That is, the processor 600 directly collects the optical signal S1 in a digital form.

In some embodiments, the processor 600 is, in an embodiment, but is not limited to, a microprocessor (uP), a digital signal processor (DSP), a microcontroller unit (MCU), or a system on chip (SoC).

Figure 5:
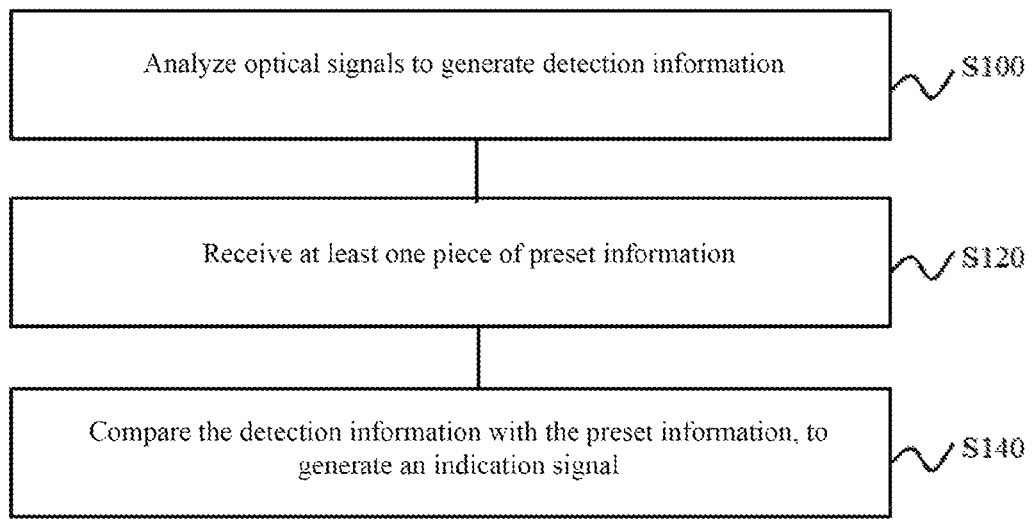
FIG. 5 is a flowchart of execution steps of a processor according to some embodiments of the disclosure.

FIG. 5 is a flowchart of execution steps of a processor 600 according to some embodiments of the disclosure. Referring to FIG. 5, in some embodiments, the processor 600 is further configured to perform the following steps, including:

Step S100: Analyze optical signals S1 to generate detection information.

Step S120: Receive at least one piece of preset information.

Step S140: Compare the detection information with the preset information to generate an indication signal S4.

According to some embodiments, when the processor 600 receives the optical signals S1, the processor 600 defines the optical signals S1 based on positions of the optical modules 200. Therefore, the processor 600 obtains a coordinate parameter (in an embodiment, an X-Y plane coordinate) of each optical signal S1 corresponding to the upper pad 100. In Step S100, the processor 600 analyzes the optical signals to obtain distance parameters between the optical modules 200 and the object, and then analyzes the distance parameters to generate the detection information.

It should be particularly noted that when there is no object on the upper pad 100, even though the optical module 200 transmits the sense signal S0, the optical signal S1 corresponding to the sense signal S0 is not generated. Therefore, the processor 600 determines whether there is a object on the upper pad 100 based on whether the processor 600 receives the optical signal S1. In addition, the processor 600 not only determines whether there is an object on the upper pad 100, but also determines an actual use area of the object on the upper pad 100 to further classify the object. Types of classification include a figure (in an embodiment, being fat or being thin) of the object and a posture type (a sitting posture, a lying posture or a yoga posture) of the object.

In some embodiments, the detection information is a weight distribution model generated by analyzing the distance parameters. That is, the processor 600 generates distribution of weight borne by the upper pad 100 based on the distance parameters and the coordinate parameter of the optical signal S1 on the upper pad 100. When the processor 600 collects sufficient data of the optical signal S1, a three-dimensional model of weight distribution of the seat cushion 10 is established.

In some embodiments, the preset information is a standard weight distribution model, that is, a standard sample corresponding to the shape and the posture type of the object. Therefore, it is determined that whether the posture of the user is appropriate by comparing the detection information with the preset information. The preset information is stored in the processor 600, a cloud device, or any electronic device with a storage.

In an embodiment, the processor 600 receives the preset information from a location such as a cloud server in which the preset information is stored, and compares the detection information with the preset information to generate the indication signal S4. When the user maintains an appropriate posture, the indication signal S4 is a positive signal. On the contrary, when the user maintains an inappropriate posture, the indication signal S4 is a negative signal. In an embodiment, the user knows whether a sitting posture is appropriate by recognizing whether the indication signal S4 is a positive signal or a negative signal.

In some embodiments, the processor 600 dynamically adjusts the preset information based on the detection information, so that the preset information is continuously optimized to keep a comparison result accurate.

Referring to FIG. 3 and FIG. 4, in some embodiments, the communications module 700 is coupled to the processor 600, and is configured to output the optical signal S1. The optical signal S1 is received and forwarded by the processor 600 from the optical module 200. In an embodiment, the communications module 700 outputs a digital optical signal S3. In other embodiments, the communications module 700 outputs the indication signal S4. The communications module 700 is but is not limited to Bluetooth, WIFI, ZigBee, another wireless transmission device, or an Ethernet transmission device.

In an embodiment, a seat cushion system includes the seat cushion 10 and an electronic device. In an embodiment, the electronic device receives the indication signal S4 from the communications module 700 to output a reminder signal. In other embodiments, the electronic device performs the foregoing steps S100 to S140 to generate the indication signal S4 after receiving the digital optical signal S3 from the communications module 700, and outputs a reminder signal based on the indication signal S4. The reminder signal is but is not limited to a sound promptly generated corresponding to the indication signal S4, a designated light turns on corresponding to the indication signal S4, or a notice promptly displays in an application (APP), to remind the user whether the sitting posture is appropriate. In addition, the electronic device outputs a corresponding reminder signal based on the indication signal S4.

In an embodiment, the seat cushion 10 further includes a battery (not shown in the figure). The battery provides power to the optical modules 200, the conversion circuit 500, the processor 600, and the communications module 700. In an embodiment, the battery is but is not limited to a disposable battery or a rechargeable battery. In an embodiment, the battery is coupled to a mains supply to be charged.

In conclusion, the seat cushion of the disclosure senses a posture of an object in a non-contact manner by the optical modules. In this way, it avoids that a sensor is easily worn out since the conventional sensor senses the object only when being in contact with the object.

Although the disclosure is described with reference to the above embodiments, the embodiments are not intended to limit the disclosure. Any person skilled in the art makes variations and modifications without departing from the spirit and scope of the disclosure. Therefore, the protection scope of the disclosure should be subject to the appended claims.

What is claimed is:

1. A seat cushion, comprising:
   an upper pad, comprising a plurality of transparent areas;
   a plurality of optical modules, located below the upper pad and disposed corresponding to the transparent areas, wherein the optical modules are configured to respectively receive an optical signal;
   a lower pad, provided with a plurality of grooves to accommodate the optical modules;
   a support structure, connected between the upper pad and the lower pad; and
   a processor, coupled to the optical modules and configured to collect the optical signals.

2. The seat cushion according to claim 1, wherein the optical modules are optical sensors and respectively comprise a transmitter and a receiver, the transmitters are respectively configured to transmit sense signals to an object, and the receivers are respectively configured to receive the optical signals reflected by the object and corresponding to the sense signals.

3. The seat cushion according to claim 2, wherein the optical sensors are time of flight (TOF) sensors, the processor respectively detects a first flight time and a second flight time by using the TOF sensors as distance parameters between the TOF sensors and the object, where the first flight time is a time required by transmitting the sense signals from the transmitters to the object and the second flight time is a time required by reflecting the optical signals from the object to the optical modules.

4. The seat cushion according to claim 2, wherein the optical sensors are structured light sensors, the sense signals and the optical signals are patterns with specific shape, and the processor analyzes differences between the patterns of the sense signals and the patterns of the optical signals by using an algorithm, to obtain depth information between each of the structured light sensors and the object as distance parameters.

5. The seat cushion according to claim 2, wherein the optical sensors are proximity sensors, and the processor analyzes differences between light energy of the sense signals and light energy of the optical signals, to obtain distance parameters between the proximity sensors and the object.

6. The seat cushion according to claim 1, wherein the optical modules are stereo vision camera modules, and the optical signals are image information.

7. The seat cushion according to claim 6, wherein each of the stereo vision camera modules comprises two or more image capture elements, configured to capture the image information of an object from different angles, and the processor performs an operation on the image information by using a triangulation method to obtain distance parameters between the stereo vision camera modules and the object.

8. The seat cushion according to claim 1, further comprising:
a conversion circuit, comprises:
a plurality of amplification circuits, respectively coupled to the optical modules, to amplify the optical signals into a plurality of amplification signals; and
a plurality of analog-to-digital circuits, respectively coupled to the amplification circuits and the processor, to convert the amplification signals into a plurality of digital optical signals, and to transmit the digital optical signals to the processor.

9. The seat cushion according to claim 1, further comprising: a communications module, coupled to the processor, and configured to output the optical signals.

10. The seat cushion according to claim 1, wherein the processor is further configured to perform the following steps:
analyzing the optical signals to generate detection information;
receiving at least one piece of preset information; and
comparing the detection information with the preset information, to generate an indication signal.

11. The seat cushion according to claim 10, wherein the processor is further configured to perform the following steps:
analyzing the optical signals to obtain a plurality of distance parameters; and
analyzing the distance parameters to obtain the detection information.

12. The seat cushion according to claim 11, wherein the detection information is a weight distribution model generated by analyzing the distance parameters.

13. The seat cushion according to claim 10, further comprising: a communications module, coupled to the processor and configured to output the indication signal.

* * * * *